(12) United States Patent
Marsh et al.

(10) Patent No.: US 9,205,269 B2
(45) Date of Patent: Dec. 8, 2015

(54) SIGNAL STRENGTH INDICATOR FOR ADJUSTING COMMUNICATION IN A MEDICAL IMPLANT

(71) Applicant: Second Sight Medical Products, Inc., San Fernando, CA (US)

(72) Inventors: David Marsh, Palmdale, CA (US); Kelly H McClure, Simi Valley, CA (US); Robert J Greenberg, Los Angeles, CA (US); Walter P Little, Tujunga, CA (US); Jordan M Neysmith, Pasadena, CA (US); Brian Coley, Vufflens-la-ville (CH); Scott Loftin, Rosamond, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 14/721,798

(22) Filed: May 26, 2015

(65) Prior Publication Data
US 2015/0273222 A1    Oct. 1, 2015

Related U.S. Application Data

(62) Division of application No. 14/040,338, filed on Sep. 27, 2013, now Pat. No. 9,042,985.

(51) Int. Cl.
*A61N 1/00* (2006.01)
*A61N 1/372* (2006.01)
*A61N 1/36* (2006.01)

(52) U.S. Cl.
CPC ........ *A61N 1/37211* (2013.01); *A61N 1/36046* (2013.01)

(58) Field of Classification Search
USPC ........................................... 607/3, 36
See application file for complete search history.

(56) References Cited

U.S. PATENT DOCUMENTS

| | | | |
|---|---|---|---|
| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,935,155 | A | 8/1999 | Humayun et al. |
| 6,400,989 | B1 | 6/2002 | Eckmiller |
| 6,458,157 | B1 | 10/2002 | Suaning |
| 2002/0046756 | A1 | 4/2002 | Laizzo et al. |
| 2007/0027505 | A1 | 2/2007 | Ginggen |
| 2008/0154337 | A1* | 6/2008 | McClure et al. ................ 607/54 |
| 2011/0106210 | A1 | 5/2011 | Meskens |

* cited by examiner

*Primary Examiner* — Nicole F Lavert
(74) *Attorney, Agent, or Firm* — Scott B. Dunbar

(57) ABSTRACT

It is critical in an inductively link medical implant, such as a visual prosthesis or other neural stimulator, to adjust the external coil to a location to maximize communication between the external coil and internal coil. Converting the signal strength between the coils to a signal easily discernible by a clinician, preferably an audible tone, facilitates the adjustment of the external coil to a preferred location.

7 Claims, 15 Drawing Sheets

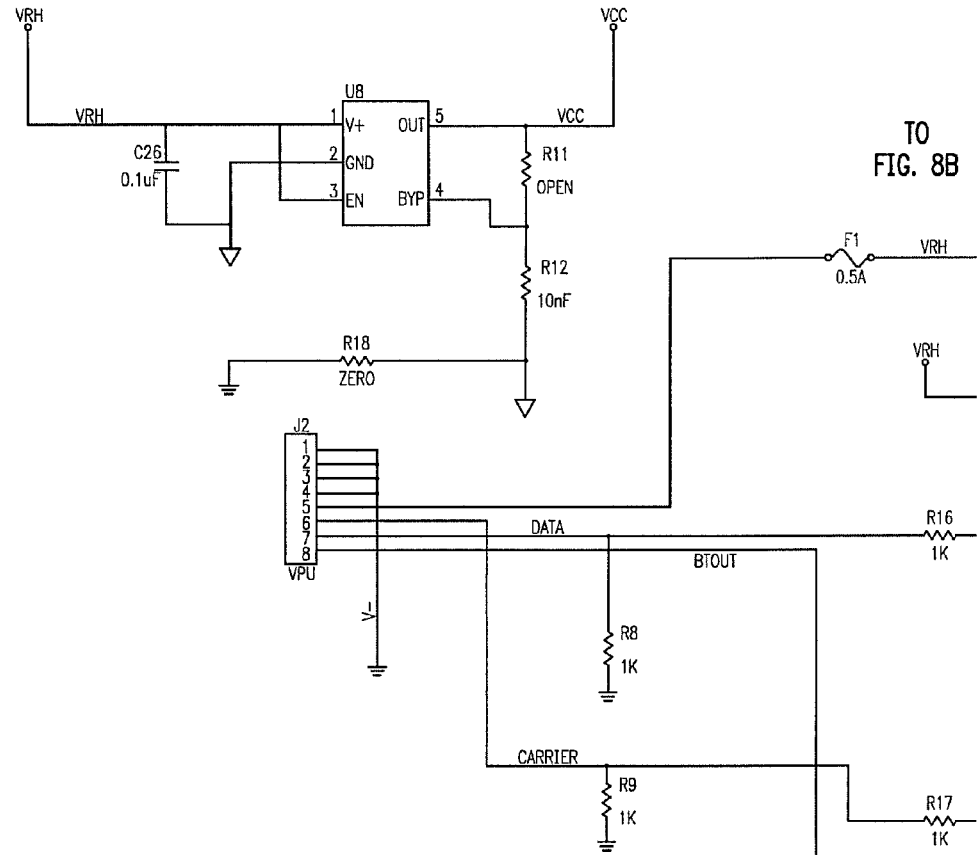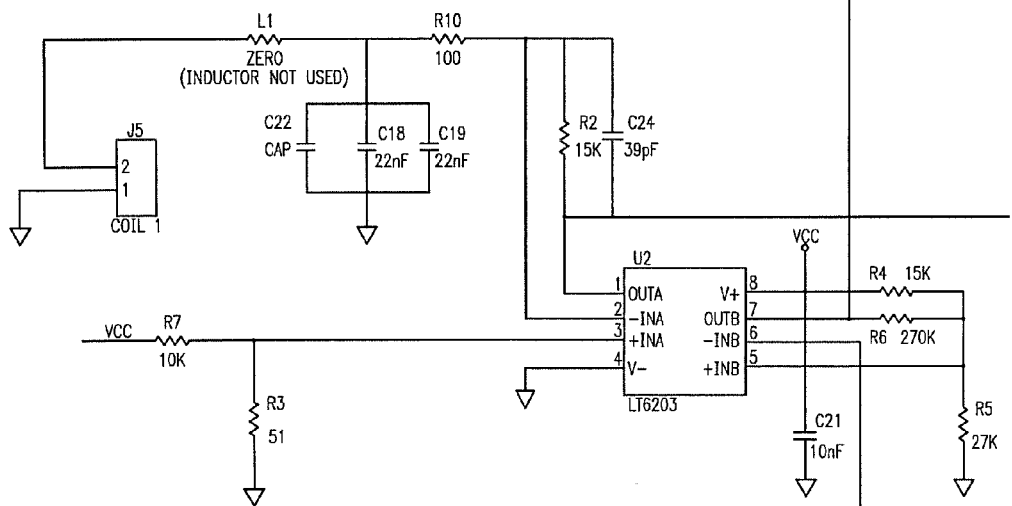
FIG. 8A

BILL OF MATERIALS

| ITEM NO. | SECOND SIGHT PART NUMBER | TITLE | QUANTITY | NOTES |
|---|---|---|---|---|
| 1 | 101055-000 | PCB, RF Board, A60 Human Trial | 1 | Assembly drawing contains Layout file |
| 2 | 100966-005 | Capacitor, 0.1uF, 50V, 0603, X7R | 7 | C1,C2,C3,C4,C5,C6,C26 |
| 3 | 100965-004 | Capacitor, 1uF, 15V, 0603, X5R | 1 | C7 |
| 4 | 100964-025 | Capacitor, 100pF, 50V, 0603, COG | 1 | C8 |
| 5 | 100964-031 | Capacitor, 180pF, 50V, 0603, COG | 1 | C9 |
| 6 | 100964-001 | Capacitor, 10pF, 50V, 0603, COG | 1 | C10 |
| 7 | 100978-002 | Capacitor, 3.3uF, 16V, 805, X5R | 2 | C11,C12 |
| 8 | 100964-021 | Capacitor, 68pF, 50V, 0603, COG | 1 | C13 |
| 9 | 100964-045 | Capacitor, 680pF, 50V, 0603, COG | 1 | C14 |
| 10 | 100966-002 | Capacitor, 10nF, 50V, 0603, X7R | 4 | C15,C20,C21,R12* |
| 11 | 100961-030 | Capacitor, 22000pF, 50V, 0605, COG | 2 | C18,C19 |
| 12 | 100967-002 | Capacitor, 6-30pF Trimmer, SMT | 1 | C23 |
| 13 | 100964-015 | Capacitor, 39pF, 50V, 0603, COG | 1 | C24 |
| 14 | 100961-TAB | Capacitor, 50V, 0805, COG | 0 | C22, Value determined after manufacturing test |
| 15 | 100961-033 | Capacitor, 12000pF, 50V, 0805, COG | 1 | C25 |
| 16 | 100967-001 | Capacitor, 3-10pF Trimmer, SMT | 1 | C27 |
| 17 | 100979-017 | Coil, 680uH, Molded, Unshielded | 1 | L4 |
| 18 | 100990-000 | Hand Wound Inductor, 280-300nH | 1 | L5 |
| 19 | 100975-152 | Resistor, 1.5K, 0603, 5%, 1/10Watt | 1 | R1 |
| 20 | 100975-153 | Resistor, 15K, 0603, 5%, 1/10Watt | 2 | R2,R4 |
| 21 | 100975-510 | Resistor, 51, 0603, 5%, 1/10Watt | 1 | R3 |
| 22 | 100975-273 | Resistor, 27K, 0603, 5%, 1/10Watt | 1 | R5 |
| 23 | 100975-274 | Resistor, 270K, 0603, 5%, 1/10Watt | 1 | R6 |
| 24 | 100975-103 | Resistor, 10K, 0603, 5%, 1/10Watt | 1 | R7 |
| 25 | 100975-102 | Resistor, 1K, 0603, 5%, 1/10Watt | 4 | R8,R9,R16,R17 |
| 26 | 100975-101 | Resistor, 100, 0603, 5%, 1/10Watt | 1 | R10 |
| 27 | 100975-473 | Resistor, 47K, 0603, 5%, 1/10Watt | 1 | R14 |
| 28 | 100975-471 | Resistor, 470, 0603, 5%, 1/10Watt | 1 | R15 |
| 29 | 100975-000 | Resistor, zero, 0603, 5%, 1/10Watt | 2 | R18,L1 |
| 30 | 100981-002 | Fuse, 0.5 Amp, 0603, Fast Acting | 1 | F1 |
| 31 | 100980-001 | Connector, 8 pos., 1.25mm header | 0 | J2 Do not install |
| 32 | 100982-001 | Diode, SOT-23, MMBD914 | 1 | D2 |
| 33 | 100983-001 | IC, FM IF System, 16-SOIC, SA604 | 1 | U1 |
| 34 | 100964-001 | IC, Operational Amplifier, 8-SOIC, LT6203 | 1 | U2 |
| 35 | 100965-001 | IC, Pin Driver, 8-SO, EL71581 | 2 | U3,U4 |
| 36 | 100986-001 | Ceramic Filter, CFXD450KCFA, SMT | 2 | U6,U7 |
| 37 | 100987-003 | IC, LDO Regulator, LP2985AIM5-4.8, SOT-23-5 | 1 | U8 |
| 38 | 100957-001 | Solder | A/R | Active Core Solder |
| 39 | 100957-002 | Solder | A/R | Rosin Core Solder |
| 40 | 130156-010 | Loctite 495 Instant Adhesive Sealant | A/R | Superglue |

FIG. 9

SIGNAL STRENGTH INDICATOR FOR ADJUSTING COMMUNICATION IN A MEDICAL IMPLANT

CROSS REFERENCE TO RELATED APPLICATIONS

This application is a divisional application of U.S. patent application Ser. No. 14/040,338, for Signal Strength Indicator for Adjusting Communications in a Medical Implant, filed Sep. 27, 2013, which claims priority to U.S. Provisional Application 61/706,253, filed Sep. 27, 2012, for Signal Strength Indicator for Adjusting Communications in a Medical Implant. This application is related to, and incorporates by reference, U.S. patent application Ser. No. 11/893,260, filed Aug. 15, 2007, entitled Visual Prosthetic Apparatus for Retinal Stimulation; U.S. patent application Ser. No. 11/598,965, filed Nov. 14, 2006, for Power Scheme for Implant Stimulator on the Human or Animal Body; and U.S. Pat. No. 8,195,303 for Video Processing Unit for Visual Prosthetic Apparatus.

FIELD

The present disclosure is generally directed to neural stimulation and more specifically to a tool for adjusting location of the coils in an inductively linked neural stimulator such as a visual prosthesis.

BACKGROUND

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., de Juan, et al., 99 Am. J. Ophthalmol. 272 (1985). These retinal tacks have proved to be biocompatible and remain embedded in the retina, with the choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

implantable neural stimulators, such as visual prostheses, must be inductively link to an outside source of power and data. The better the link between the two coils, the less power is require to operate the neural stimulator. Since the internal coil is fixed at the time of implantation, all adjustment must be made to the external coil. Systems are needed to quickly identify the optimal position for the external coil and to hold the external coil in that position for use.

SUMMARY

It is critical, in an inductively linked medical implant, to adjust the external coil to a location to optimize communication between the external coil and internal coil. Examples include a visual prosthesis or other neural stimulator. Converting the signal strength between the coils to a signal indicator easily discernible by a clinician preferably an audible tone facilitates the adjustment of the external coil to a preferred location. Specifically, the return signal from the internal (implanted) coil to the external coil is generally weaker than the signal from the external coil to the internal coil. Hence, converting the return signal to an audible tone, or other indicator (visual display of coil alignment or signal level etc.) helps properly locate the external coil.

A first aspect of the present invention is converter and speaker which generates an audible tone with a frequency proportional to signal strength, which can be connected to the RF circuitry of the external portion of a medical implant.

A second aspect of the present invention is a method of adjusting the mounting of an external coil while listening to an audible tone to maximize the signal between the internal and external coils.

BRIEF DESCRIPTION OF THE DRAWINGS

FIGS. 8A and 8B (to be viewed side by side) show a circuital diagram of RF circuitry 17 shown in FIG. 4.

FIG. 9 shows a table with exemplary values for the components of the circuit of FIGS. 8A and 8B.

DETAILED DESCRIPTION

Figure 1:
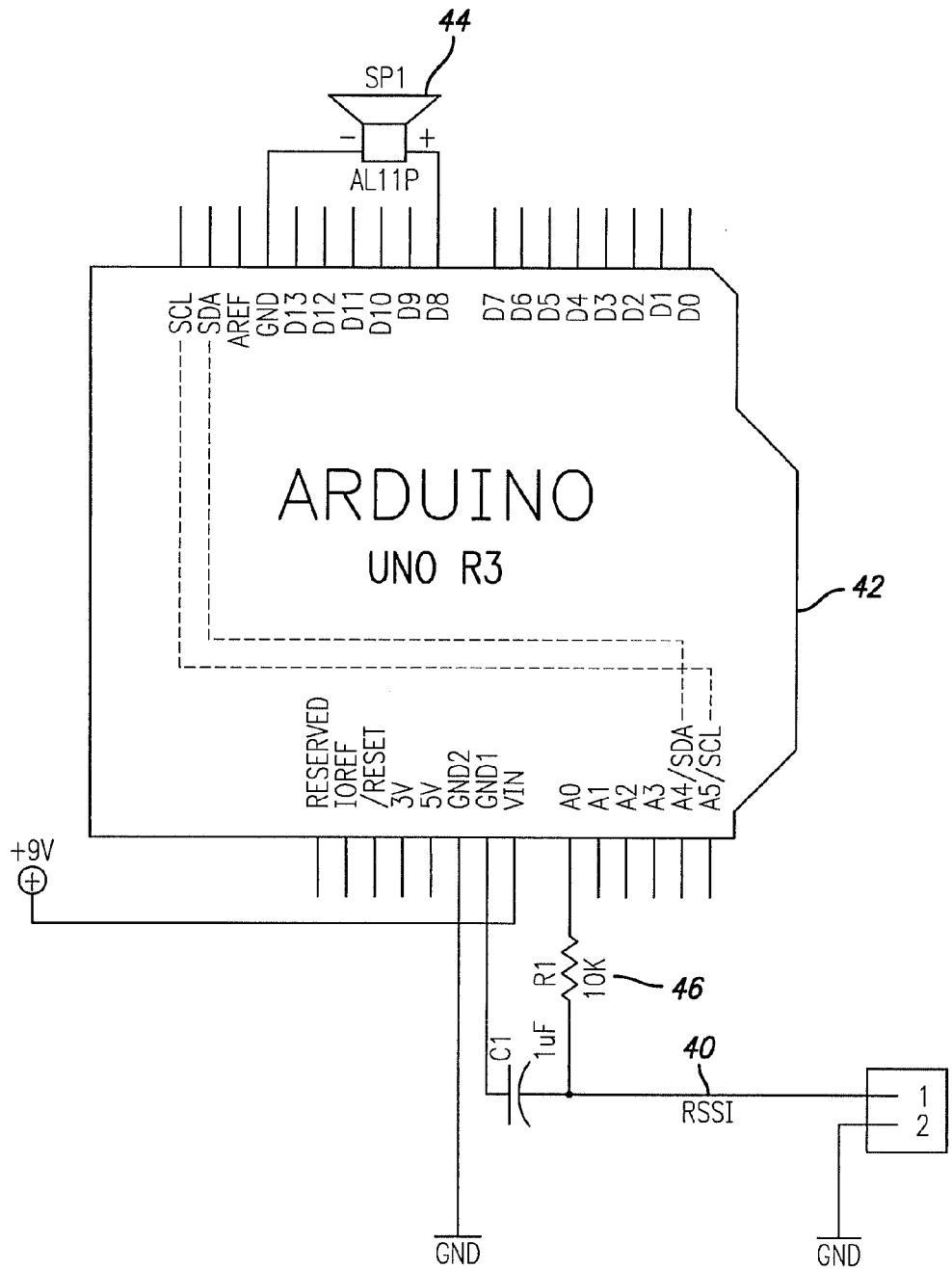
FIG. 1 is a schematic of the signal strength indicator.

FIG. 1 is a schematic of the signal strength indicator according to the present invention. The signal strength indicator provides an audible signal with a frequency proportional to signal strength from a telemetry signal from an implanted visual prosthesis. A received signal strength indication (RSSI) signal 40 is received by a signal strength indicator microprocessor 42. RSSI is an IEEE 802.11 standard signal commonly produced by receiver chips ranging from 2.8V to 4.1V. The source of the RSSI signal 40 is discussed below with respect to FIG. 8B. A filter circuit 46 filters the RSSI signal 40 before the signal strength microprocessor 42. The signal strength microprocessor 42 converts the RSSI signal 40 to a frequency signal with pitch proportional to the value of the RSSI signal 40. The output of the signal strength indicator microprocessor is sent to a speaker 44 to output the signal in an audible form. A clinician can adjust an external coil 4 while listening to the output of speaker 44 to find the optimal position for the external coil 4. The preferred embodiment as set forth in the present disclosure describes a visual prosthesis. One skilled in the art would understand how the present invention may be adapted to a wide range of implantable devices which require a good link between external and internal coils.

The signal strength indicator microprocessor 42 runs the following program to convert the RSSI signal 40 to an audible tone.

```
/*
RSSI audio feedback system
Written for Arduino Uno
Analog input R/C filtered ~159 Hz cutoff (10K&.1uF)
Filters input samples with FIR
DJM 09/08/12
*/
const int freq_out=13; // scope pin frequency out
const int speaker_out=8; // tone output pin
const int lowrange=600; // ~2.8V-1023 at full-scale 5V ref
const int hirange=818; // ~4V
const int tonelow=800; // bottom tone out range in Hz
const int tonehigh=1800; // top tone out range in Hz
double decay=0.995522; // exp(-2.0 * PI * (transition freq=2 Hz)/(sample rate=2800 Hz))
double amplitude=1.0- decay;
int pinstate=1;
double movingavg=0.0;
double sample;
int tonefreq;
void setup( ){
// initialize the digital pin as an output.
pinMode(freq_out, OUTPUT);
pinMode(speaker_out, OUTPUT);
pinMode(9,OUTPUT);
digitalWrite(9,HIGH);
}
// the following loop is measured to run at about 2800 Hz via the freq_out pin while tone out active, 6 KHz silent
void loop( ){
pinstate^=1; // pulses at ½ loop rate
digitalWrite(freq_out, pinstate);
// Sample & filter
sample=analogRead(0);
movingavg *=decay;
movingavg+=amplitude*sample;
// tone frequency proportional to RSSI
// no sound if no implant detected
if(movingavg>lowrange) {
tonefreq=map(movingavg,lowrange,hirange,tonelow,tonehigh);
tone(speaker_outtonefreq);
}else{
noTone(speaker_out);
}
```

Figure 2:
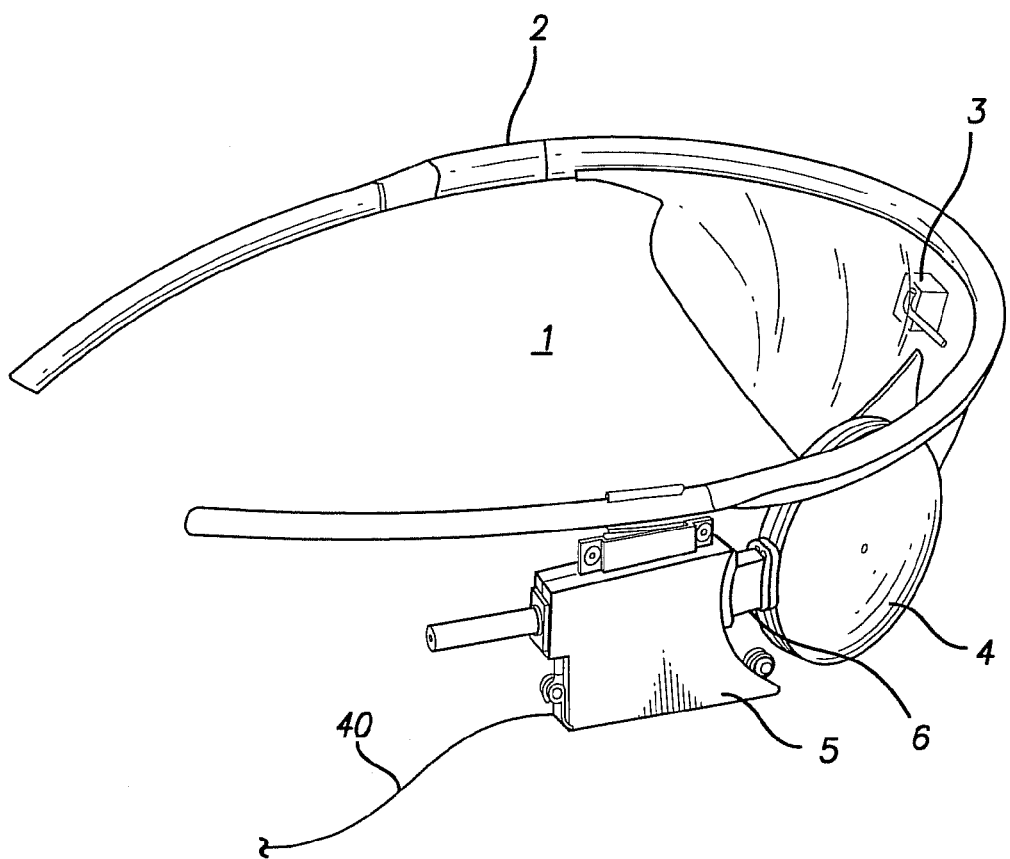
FIGS. 2 and 3 show perspective views of an external portion of a visual prosthetic apparatus.
Figure 3:
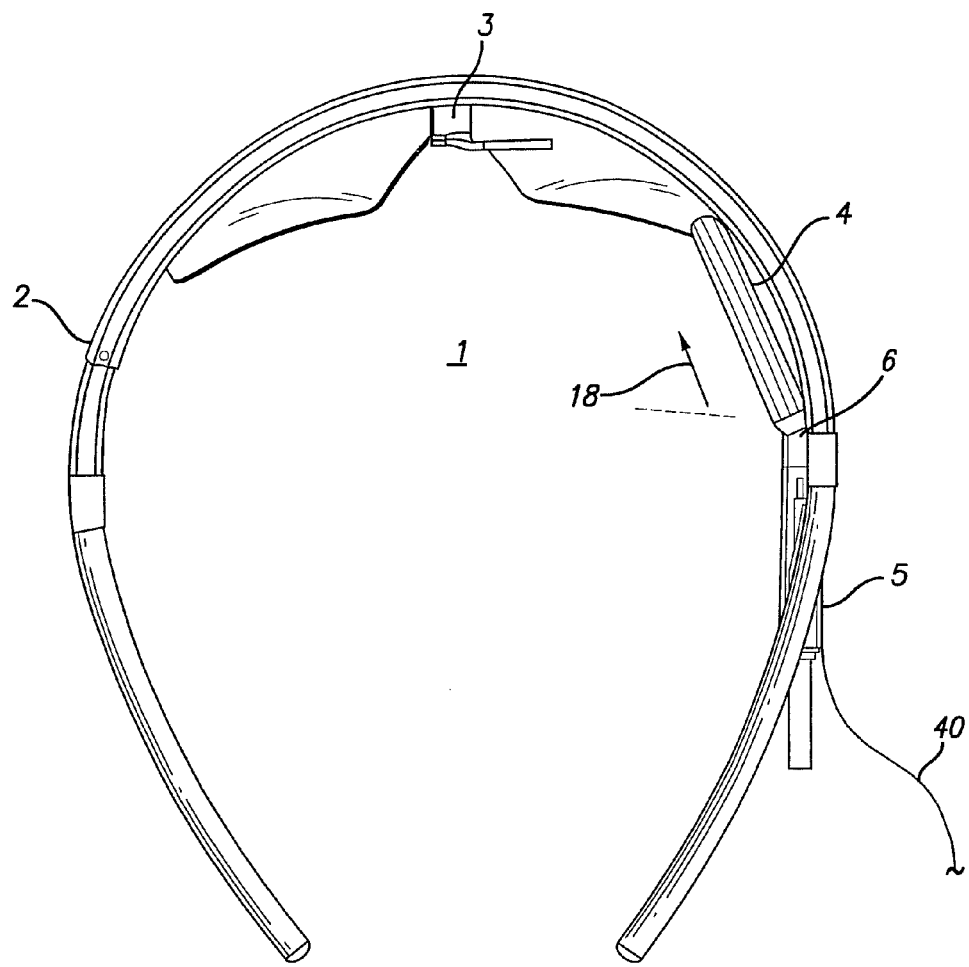

FIGS. 2 and 3 show two different perspective views of an external portion of a visual prosthetic apparatus according to the present disclosure. 'External' is here meant to indicate that the portion is external to the human body, and not implanted therein. The external portion is adapted to be used in combination with an implantable portion 23, shown in FIGS. 6 and 7. Turning to FIGS. 2 and 3, the external portion comprises a frame 2 holding a camera 3, an external coil arrangement 4 and a mounting system 5 for the external coil arrangement 4. The external coil arrangement 4 comprises external transmitting and receiving radio-frequency (RF) coils (later shown in FIG. 4) adapted to be used together and communicate with an internal RE coil (later shown in FIGS. 6 and 7). The mounting system 5 also encloses the RF circuitry 17 (see FIG. 4) for modulating, demodulating, transmitting, and receiving an RF signal. External coil arrangement 4 and mounting system 5 are connected by a flexible connector 6.

Figure 4:
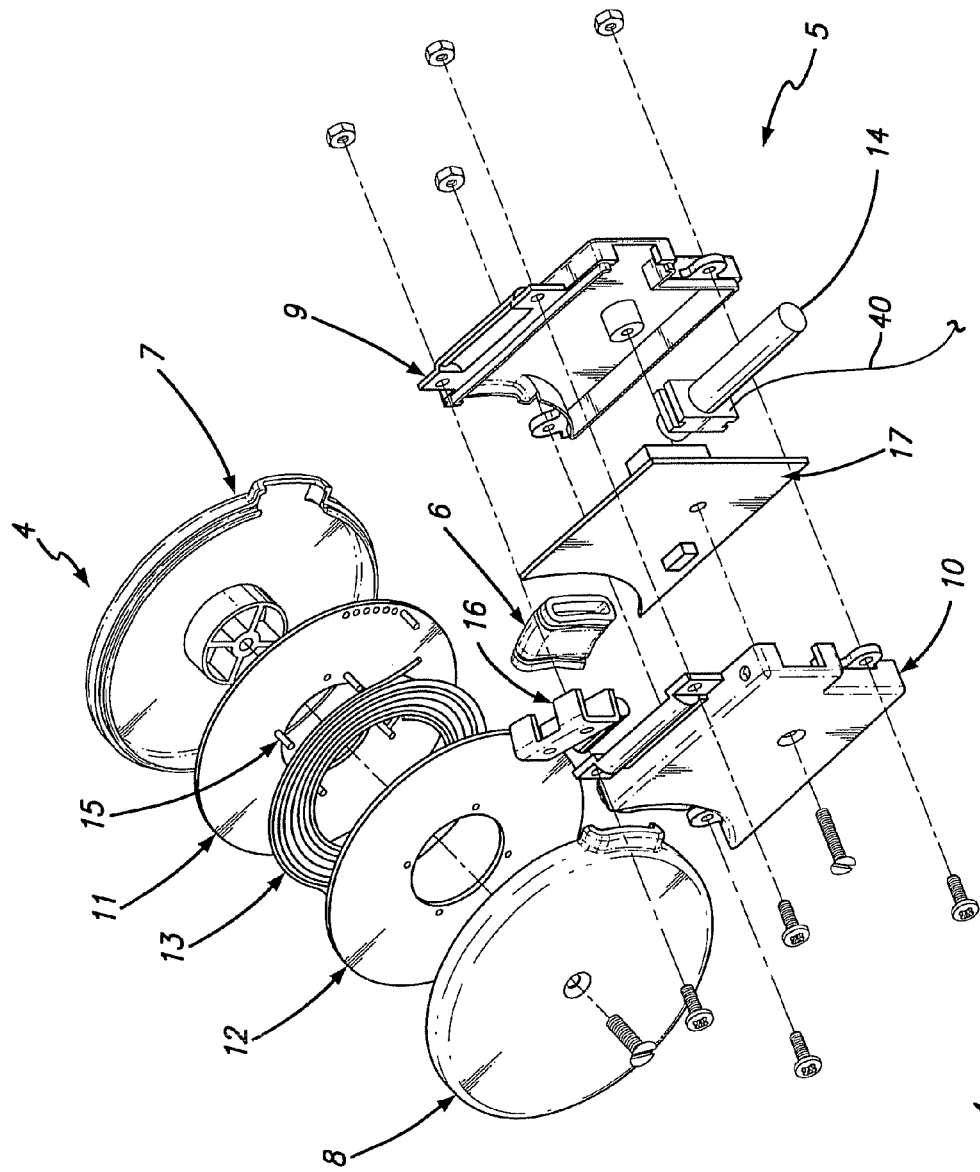
FIG. 4 is an exploded view of the external coil arrangement and mounting system shown in FIGS. 2 and 3.
Figure 8B:
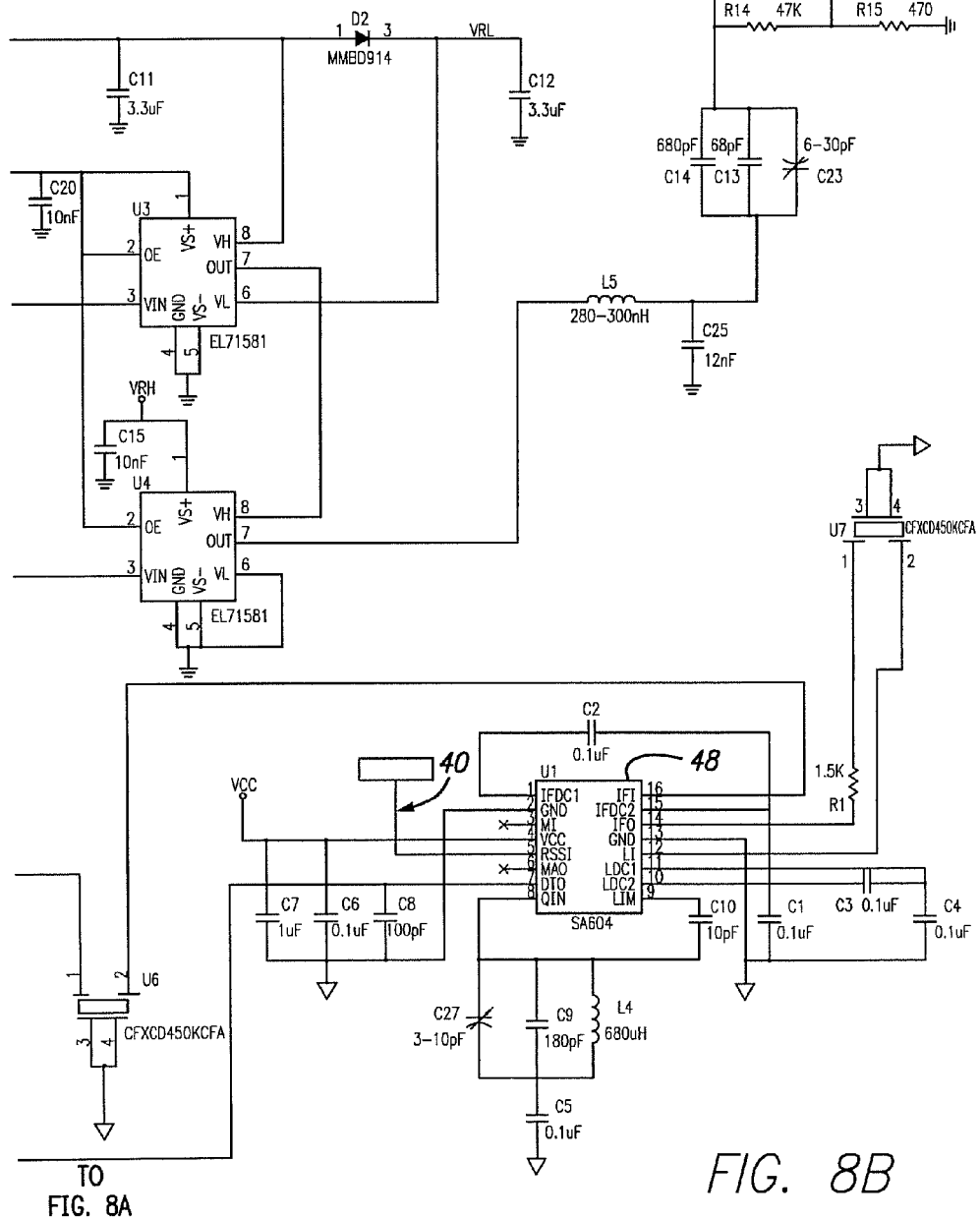
Figure 10:
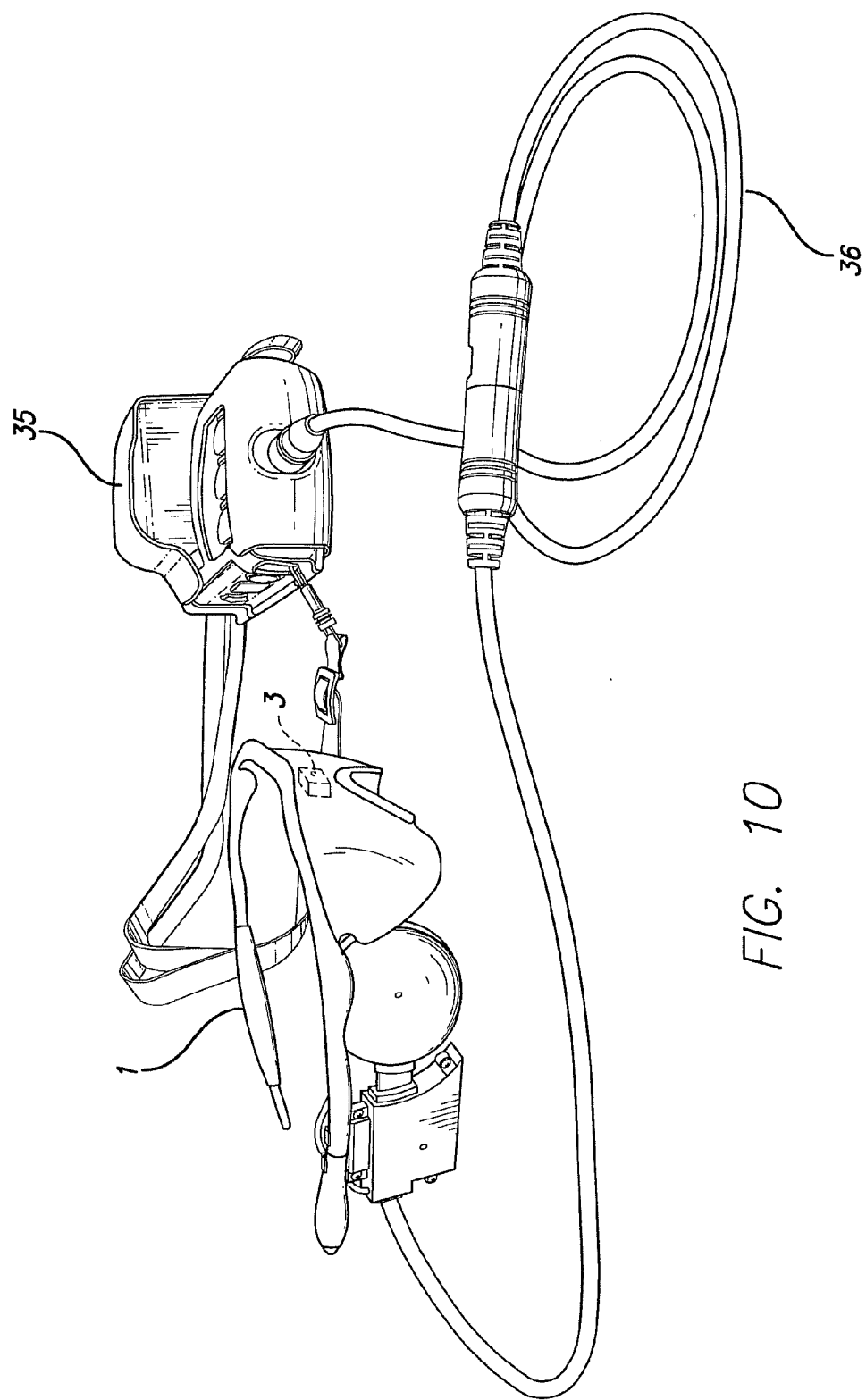
FIG. 10 shows an arrangement comprising a visor, a visual processing unit and a cable connecting the visor to the visual processing unit.

FIG. 4 shows an exploded view of the external coil arrangement 4 and mounting system 5. As also shown in FIGS. 2 and 3, the external coil arrangement 4 and mounting system 5 are connected by a flexible connector 6. In particular, the flexible connector 6 is attached to RF coil enclosure halves 7 and 8 on the coil side and to enclosure case halves 9 and 10 on the mounting system side. The external coil arrangement 4 comprises coil enclosure halves 7 and 8, enclosing printed circuit boards (PCB) 11 and 12 surrounding an RF transmitting coil 13. The PCBs 11 and 12 further include telemetry receiving coils. The mounting system 5 comprises case halves 9 and 10 enclosing an RF visor cable assembly 14. A separate cable assembly and connector is provided for the RSSI signal 40. The RSSI cable is only connected to the RE circuitry housing 10 when adjusting the coil mounting system 6, and is then disconnected. Other mechanical components shown in FIG. 4 include: wires 15 connecting PCBs 11 and 12; a mounting bracket 16 (later described in FIG. 5); and RF circuitry 17 located between case halves 9 and 10. While video image processing is done in a remote video processing unit (shown in FIG. 10), the RF circuitry 17 is incorporated into the mounting system 5 to reduce losses in the cable connecting the video processing unit to the glasses. PCBs 11 and 12 can be made of glass base epoxy and laminated with copper. An exemplary circuital diagram of RF circuitry 17 is shown in FIGS. 8A, 8B and 9. FIG. 10 shows an arrangement comprising a visor 1 connected to a visual processing unit(VPU) 35 through a cable 36.

Figure 6:
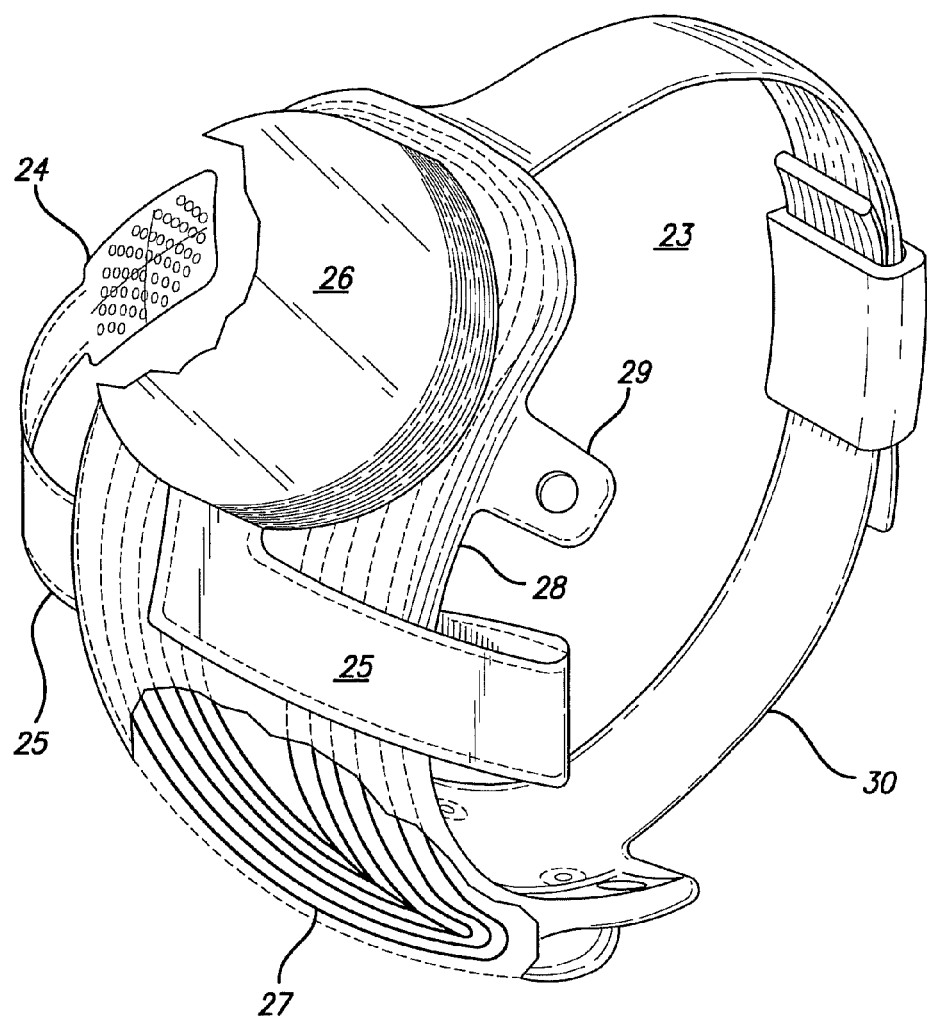
FIG. 6 shows a perspective view of the implantable portion of the visual prosthesis.
Figure 7:
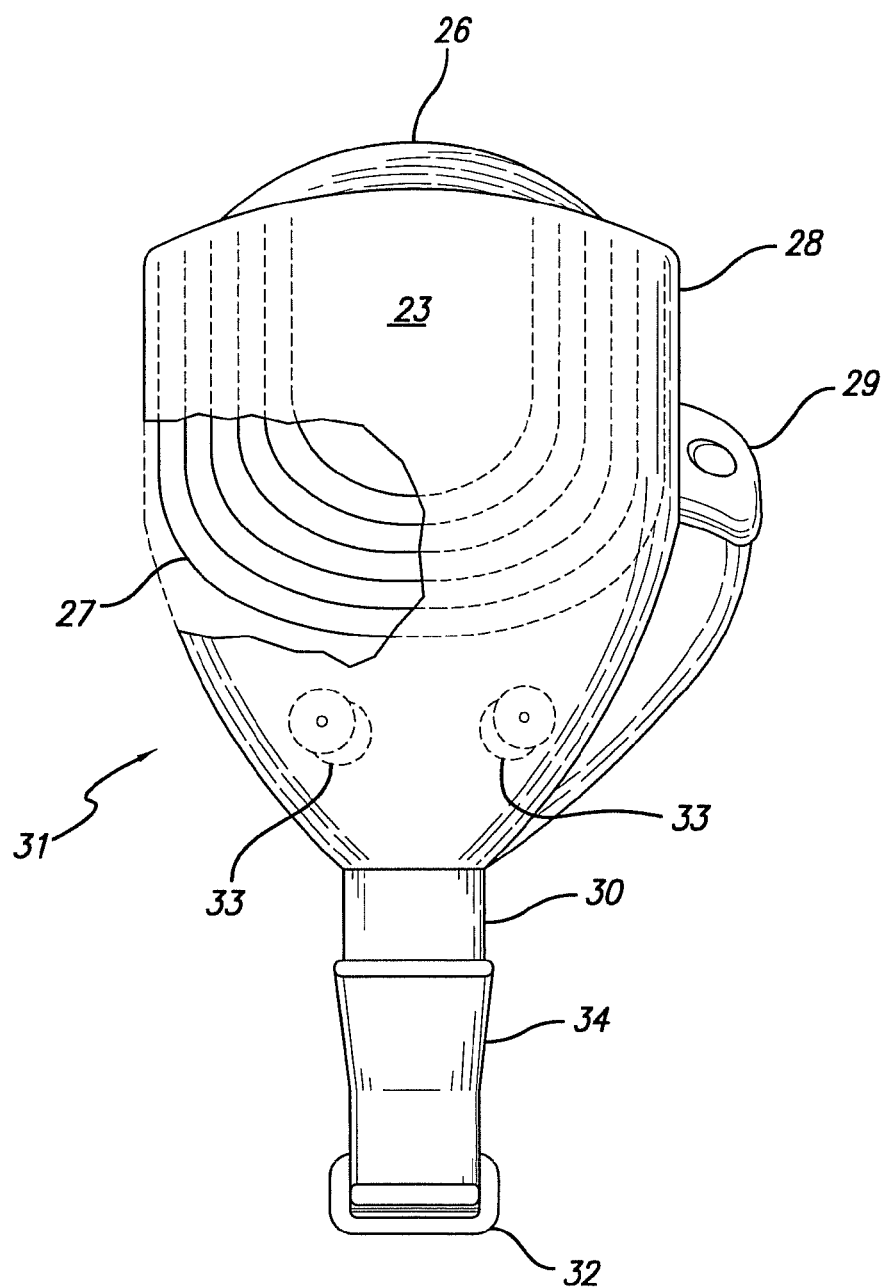
FIG. 7 is a side view of the implantable portion of the visual prosthesis.

Three structural features are provided in the visual prosthesis to control the distance, and thereby reduce the distance, between the external coil 13 (included in arrangement 14) and the inductive (implanted) coil (27, FIGS. 6 and 7). The three structural features correspond to movement of the external coil along the three possible spatial axes occupied by the two coils. That is, the external and inductive coils can be viewed as being separated in anatomical axes: the medial-lateral, superior-inferior, and the anterior-posterior axis. Control of the distance between external coil 13 and implanted coil 27 is important, because it allows a better signal transmission via the 13-27 inductive coupling.

The first structural feature is adapted to reduce the distance between the coils along the medial-lateral axis by bending the external coil arrangement 4, thus bending the external coil 13. The distance in this medial-lateral axis should be equivalent to the separation distance of the coils if the centers of the coils are aligned. The enclosure 4 of the external coil 13 is attached to the mounting system 5, which is attached to the leg frame 2 of the visual apparatus. While the RF circuitry within the mounting system 5 is in line with the leg frame 2, the external coil 13 has been given a preferential bend 18 towards the face using the flexible connector 6 shown in FIG. 4. With the external coil 4, 13 angled toward the face (e.g., at 25 degrees) (see FIGS. 2 and 3), the external coil 4, 13 makes contact with the subject's face and the flexible connector allows conformation to the subject's facial contours. Thus, the external coil 4, 13 is brought in as close as possible in the medial-lateral axis for the subject.

The second structural feature is a sliding bar mechanism adapted to control movement of the external coil 4, 13 along the anterior-posterior axis. The point at which the mounting system 5 connects to the visor allows for adjustment along this anterior-posterior axis (e.g., a 7 mm adjustment). The sliding bar mechanism can be fixed in place when the optimal position is found by tightening two screws on the sides of the sliding bar.

Figure 5:
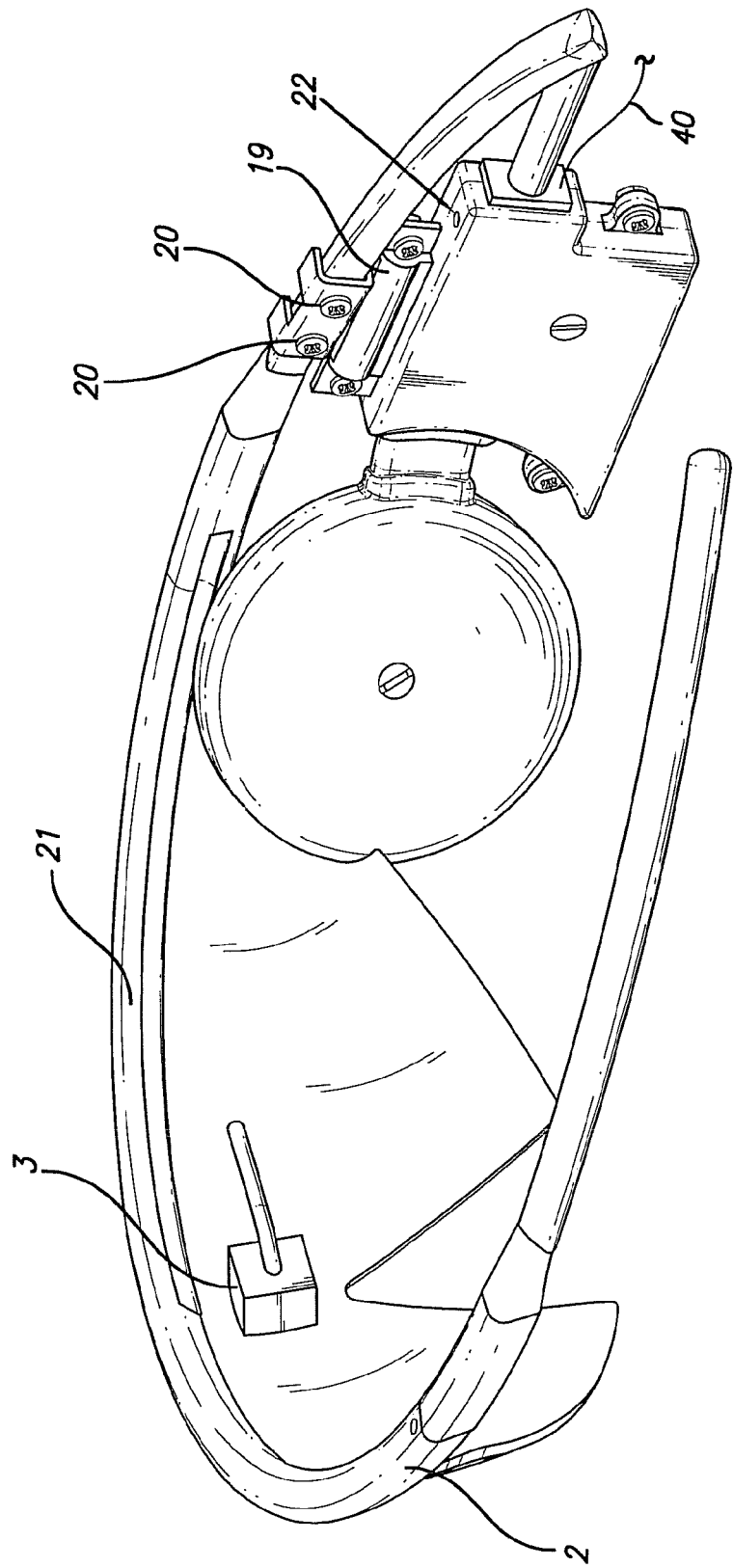
FIG. 5 is a further perspective view of the external portion of the visual prosthetic apparatus.

In particular, reference can be made to FIG. 5, which shows a further perspective view of the apparatus shown in FIGS. 2 and 3. In particular, FIG. 5 shows a sliding bar mechanism 19 which is tightened into position by screws 20. FIG. 5 also shows a trench 21 for routing camera cable connected to the camera 3. The camera cable end can be inserted into hole 22 of the mounting system 5.

The third structural feature is adjustment of the position of the external coil 4, 13 along the superior-inferior axis by varying the placement of the visual apparatus 1 along the subject's nose. When the visual apparatus 1 is worn close to the face, the external coil 13 is higher, and when worn further from the face, the external coil 13 is lower. Using these three structural adjustments alone or in combination, the coil separation distance can be adjusted to obtain an optimal RF link for individual subjects.

FIG. 6 shows a perspective view of an implantable portion 23 of a retinal prosthesis as disclosed. An electrode array 24 is mounted by a retinal tack or similar means to the epiretinal surface. The electrode array 24 is electrically coupled by a cable 25, which can pierce the sclera and be electrically coupled to an electronics package 26 external to the sclera. Electronic package 26 includes the RF receiver and electrode drivers.

The electronics package 26 can be electrically coupled to the secondary inductive coil 27. In one aspect, the secondary inductive coil 27 is made from wound wire. Alternatively, the secondary inductive coil may be made from a thin film polymer sandwich with wire traces deposited between layers of thin film polymer. The electronics package 26 and secondary inductive coil 27 are held together by a molded body 28. The molded body 28 may also include suture tabs 29. The molded body narrows to form a strap 30 which surrounds the sclera and holds the molded body 28, secondary inductive coil 27, and electronics package 26 in place. The molded body 28, suture tabs 29 and strap 30 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the secondary inductive coil 27 and molded body 28 are oval shaped, and in this way, a strap 30 can better support the oval shaped coil.

The entire implantable portion 23 is attached to and supported by the sclera of a subject. The eye moves constantly. The eye moves to scan a scene and also has a jitter motion to prevent image stabilization. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 7 shows a side view of the implantable portion of the retinal prosthesis, in particular, emphasizing the fan tail 31. When the retinal prosthesis is implanted, the strap 30 has to be passed under the eye muscles to surround the sclera. The secondary inductive coil 27 and molded body 28 should also follow the strap under the lateral rectus muscle on the side of the sclera. The implantable portion 23 of the retinal prosthesis is very delicate. It is easy to tear the molded body 28 or break wires in the secondary inductive coil 27. In order to allow the molded body 28 to slide smoothly under the lateral rectus muscle, the molded body is shaped in the form of a fan tail 31 on the end opposite the electronics package 26. Element 32 shows a retention sleeve, while elements 33 and 34 show holes for surgical positioning and a ramp for surgical positioning, respectively.

FIGS. 8A and 8B show a schematic diagram of RF circuitry 17 shown in FIG. 4. For purposes of the present invention is important to note that a receiver processor 48 receives a very weak telemetry signal. For adjusting the external coil 4, it is only necessary to track the telemetry signal as it is much weaker than the forward data signal. The receiver processor 48 produces the RSSI signal 40 discussed with respect to FIG. 1. The RSSI signal 40 is a standard feature of many commercially available receiver processors. FIG. 9 shows a table with exemplary values for the components of the circuit of FIGS. 8A and 8B.

FIG. 10 shows an arrangement comprising a visor, a visual processing unit and a cable connecting the visor to the visual processing unit. This is as the device is used in stand-alone mode. The signal strength indicator would not be connected to the visual prosthesis as used by a patient. The visor 1, as described above is connected by a cable 36 to a video processing unit 35 as worn by the patient.

Figure 11:
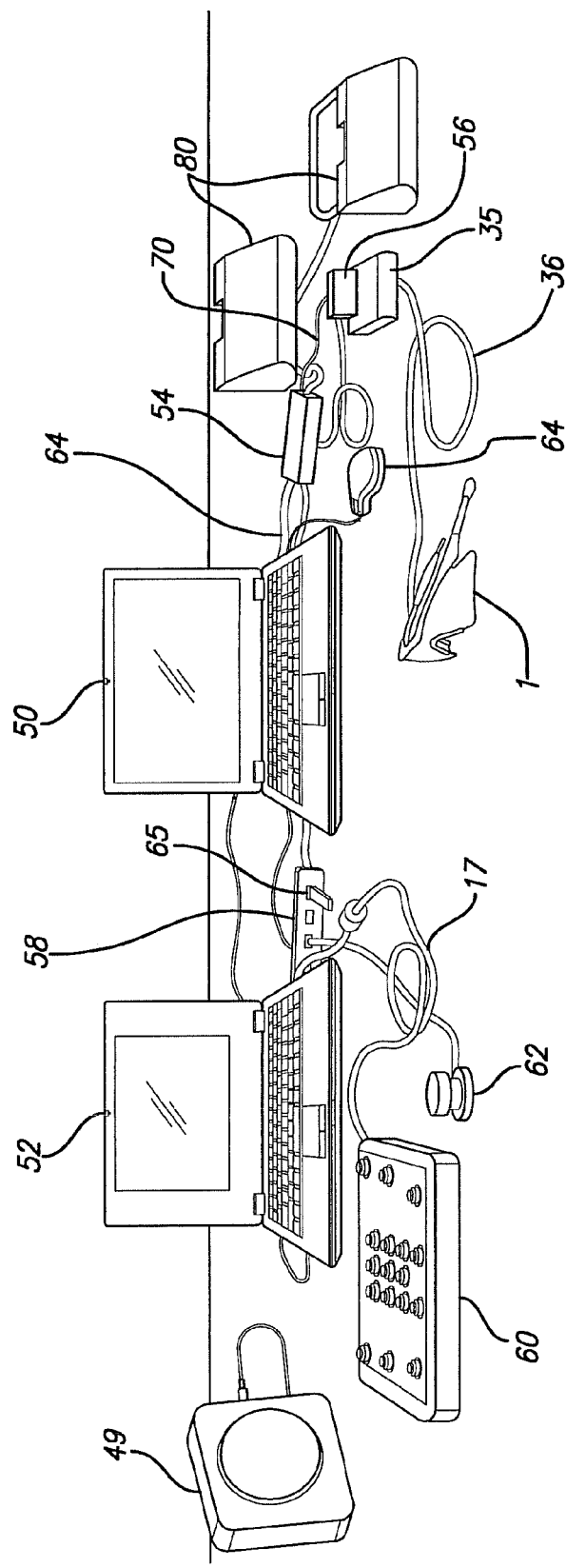
FIG. 11 shows components of a fitting system according to the present disclosure, the system also comprising the visor shown in FIGS. 6A-6B and 7.

Referring to FIG. 11, a Fitting System (FS) may be used to configure and optimize the visual prosthesis apparatus shown in FIGS. 1-10. In this case an alternative signal strength indicator may be used. Signal strength data may be passed back to a fitting system laptop 50 and the signal strength indicator incorporated into the fitting system software.

The Fitting System may comprise custom software with a graphical user interface running on a dedicated laptop computer 50. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 35 discussed above and store it in non-volatile memory to control various aspects of video configuration, e.g. the spatial relationship between the video input and the electrodes. The software can also load a previously used video configuration file from the VPU 35 for adjustment.

The Fitting System can be connected to the Psychophysical Test System (PTS), located for example on a dedicated laptop 52, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the retinal prosthesis for each subject.

The Fitting System laptop 50 of FIG. 11 may be connected to the VPU 35 using an optically isolated serial connection adapter 54. Because it is optically isolated, the serial connection adapter 54 assures that no electric leakage current can flow from the Fitting System laptop 50 in the even of a fault condition.

As shown in FIG. 11, the following components may be used with the Fitting System according to the present disclosure. The Video Processing Unit (VPU) 35 for the subject being tested, a Charged Battery 56 for VPU 35, the Glasses 1, a Fitting System (FS) Laptop 50, a Psychophysical Test System (PTS) Laptop 52, a PTS CD (not shown), a Communication Adapter (CA) 54, a USB Drive (Security) (not shown), a USB Drive (Transfer) 65, a USB Drive (Video Settings) (not shown), a Patient Input Device (RF Tablet) 60, a further Patient Input Device (Jog Dial) 62, Glasses Cable 36, CA-VPU Cable 70, FS-CA Cable 64, FS-PTS Cable, Four (4) Port USB Hub 58, Mouse 64, Test Array system 80, Archival USB Drive 49, an Isolation Transformer (not shown), adapter cables (not shown), and an External Monitor (not shown).

With continued reference to FIG. 11, the external components of the Fitting System may be configured as follows. The battery 56 is connected with the VPU 35. The PTS Laptop 52 is connected to FS Laptop 50 using the FS-PTS Cable. The PTS Laptop 52 and FS Laptop 50 are plugged into the Isolation Transformer (not shown) using the Adapter Cables (not shown). The Isolation Transformer is plugged into the wall outlet. The four (4) Port USB Hub 58 is connected to the FS laptop 50 at the USB port. The mouse 64 and the two Patient Input Devices 60 and 62 are connected to four (4) Port USB Hub 58. The FS laptop 50 is connected to the Communication Adapter (CA) 54 using the FS-CA Cable 64. The CA 54 is connected to the VPU 35 using the CA-VPU Cable 70. The Glasses 1 are connected to the VPU 35 using the Glasses Cable 36.

In one exemplary embodiment, the Fitting System shown in FIG. 11 may be used to configure system stimulation parameters and video processing strategies for each subject outfitted with the visual prosthesis apparatus of FIG. 10. The fitting application, operating system, laptops 52 and 52, isolation unit and VPU 35 may be tested and configuration controlled as a system. The software provides modules for electrode control, allowing an interactive construction of test stimuli with control over amplitude, pulse width, and frequency of the stimulation waveform of each electrode in the Retinal stimulation system shown in FIGS. 6 and 7. These parameters are checked to ensure that maximum charge per phase limits, charge balance, and power limitations are met before the test stimuli are presented to the subject. Additionally, these parameters may be checked a second time by the VPU 35's firmware.

Once the VPU 35 is connected to the Fitting System laptop 50 through the communications adapter 54, signal strength data may be passed back to a fitting system laptop 50 and the signal strength indicator incorporated into the fitting system software. The most straight forward method is to pass the RSSI signal back to the fitting system laptop 50 encoded within the digital signal. Then various signal strength indicators are possible. An audible tone with frequency matched to the RSSI signal can be played through the fitting system laptop 50 speaker. A graphical representation of a signal strength meter can be displayed on the fitting system laptop 50 display. Various other displays are possible including charts or bar graphs indicating the distance of the external coil from the optimal position.

The VPU 35 tracks and returns to the fitting system laptop 50 many parameters of visual prosthesis performance in the form of an event log. These additional parameters can be incorporated into a signal strength indicator. This can be used to indicator the quality of the link over time. The VPU appends these parameters to its event log when it is powered down that give aggregate measurements used in calculating a percentage of time link between the internal and external coils:

RF_LINK_EXPECTED_TIME_S is the time in seconds for which RF link could have been available (i.e. this number is basically the duration of time that the VPU was powered on, minus a very brief period to account for the VPU booting up).

RF_LINK_MISSING_WHEN_EXPECTED_TIME_S is the time in seconds that the coils didn't have link.

Simple division of these two parameters yields the percentage of link loss between the coils. The VPU 35 also saves parameters that indicate how many times the system lost and restored link. All of this data can be combined to provide a better indication of signal strength over time.

If the VPU 35 calculates the percentage of link loss, it and/or the fitting system laptop 50 can alert the clinician if the percentage is higher than the spec (i.e. a warning along the lines of "The system's RF link is poor, please adjust") so that the clinician can pursue further adjustment/optimization.

This can be at the start of a testing session based whatever data is present in the VPU 35, or can be ongoing in real-time.

The signal strength meter can be useful in adjusting additional parameters, other than coil alignment. Two additional parameters are adjustable—Back Telemetry Power and RF Link Tolerance. Back Telemetry Power corresponds with a 2-bit parameter in the VPU 35 processor chip and can be set to 200 uA, 400 uA, 600 uA, or 800 uA, with a default of 600 uA. The VPU can also provide an adjustable parameter of RF Link Tolerance. This parameter adjusts the number of bad (invalid parity) or missing Back Telemetry frames the VPU will allow before considering link to be lost and attempting to re-link. Increasing this tolerance should help the overall link percentage when there is a situation of frequent but very brief going in and out of link. The default setting is 13 frames (8.3 ms per frame) and it can be configured to any value between 0 and 50 frames. The clinicians may increase or decrease the link loss tolerance or Back Telemetry Power depending on information from the signal strength meter.

Additional it is possible to provide a "Fix it for me" option in a warning message that would automatically adjust these parameters, evaluate the effect, and converge on the best settings, under control of the fitting system software.

It is further possible to use other data, for example if an RSSI signal is not available, in this alternate embodiment. The power management system within the implanted portion uses a capacitive storage arrangement with a shunt regulator. Shunt current is sent from the implanted portion of the visual prosthesis to the VPU 35 to control power sent by the VPU 35 to the implanted portion of the visual prosthesis. This information is relayed to the fitting system laptop 50. This can be converted to a signal strength indicator.

The fitting system laptop 50 can output a sine-wave tone with a frequency based on measurements received from the VPU 35. The formula for determining the output frequency is as follows:

$$Fout=round(Fmin+((Fmax-Fmin)/MAX\_DIFF*(MAX\_DIFF-(Vrf+abs(RfNom-Isrh)))))$$

where:
Fout—the resulting output frequency, in Hertz (Hz)
Fmin—the minimum output frequency, 440 Hz
Fmax—the maximum output frequency, 1760 Hz
MAX_DIFF—the maximum possible sum of Vrf and the absolute value of the difference of RfNom and Isrh, this is a constant of 88 (from worst case scenario of Vrf=31 and abs (RfNom−Isrh)=57).
Vrf—the RF voltage reading from the VPU, in digital units, 0 to 31
RfNom—the RF nominal value, set in the VPU, in digital units, 1 to 58
Isrh—Shunt regulator current (high side) reading from the VPU, in digital units, 1 to 58

The rationale behind this formula is that, when lacking access to a true signal strength measurement (e.g. RSSI), the fitting system laptop 50 can provide a reasonable approximation by considering the theoretical best case for coil placement—that the Isrh is equal to the RF nominal value, and RF Voltage required to accomplish this current level is as low as possible (digital 0=4.5 V).

Figure 12A:
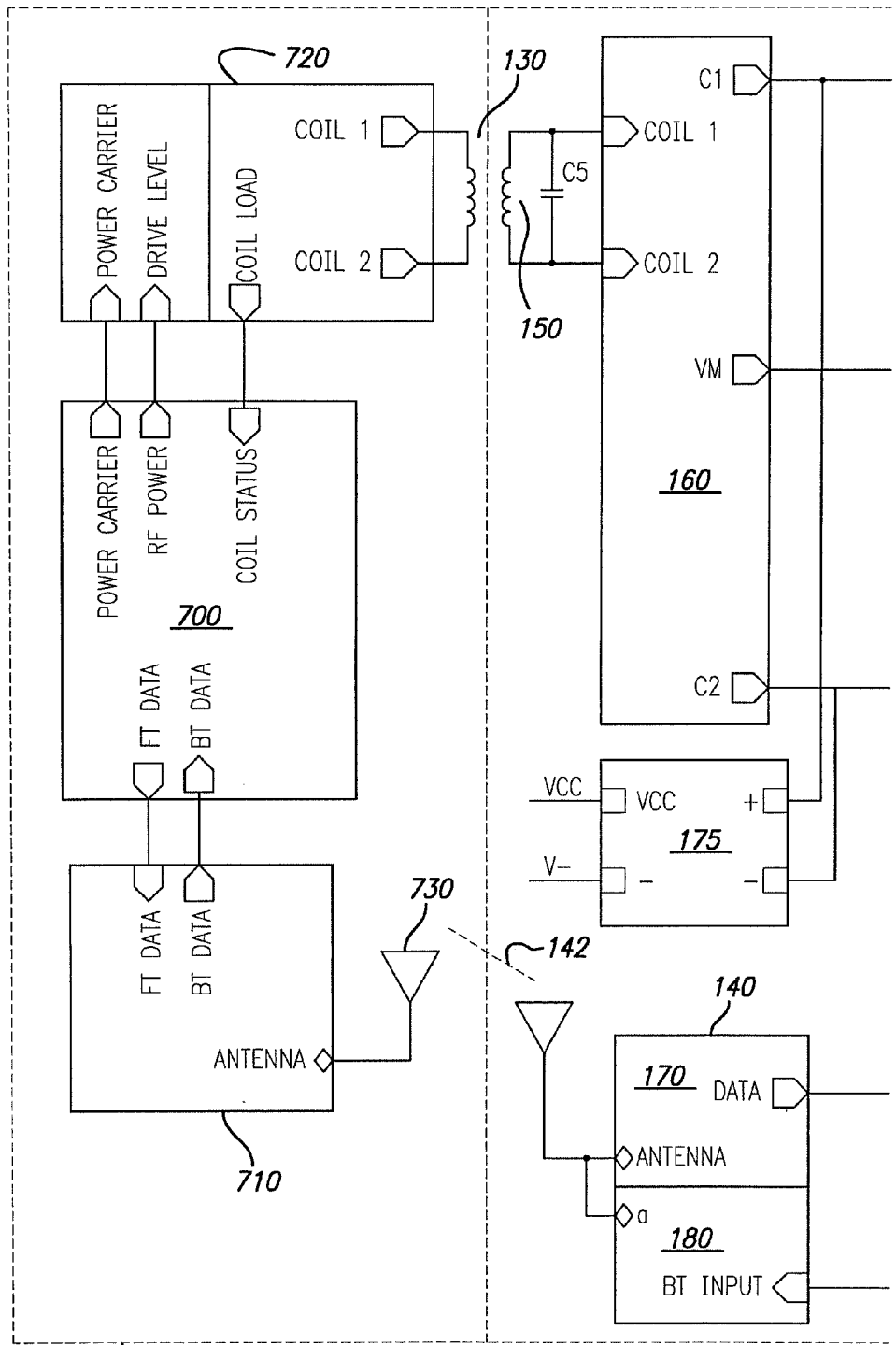
FIGS. 12A, 12B, and 12C show a general diagram of the implant power control scheme which provides shunt regulator current.
Figure 12B:
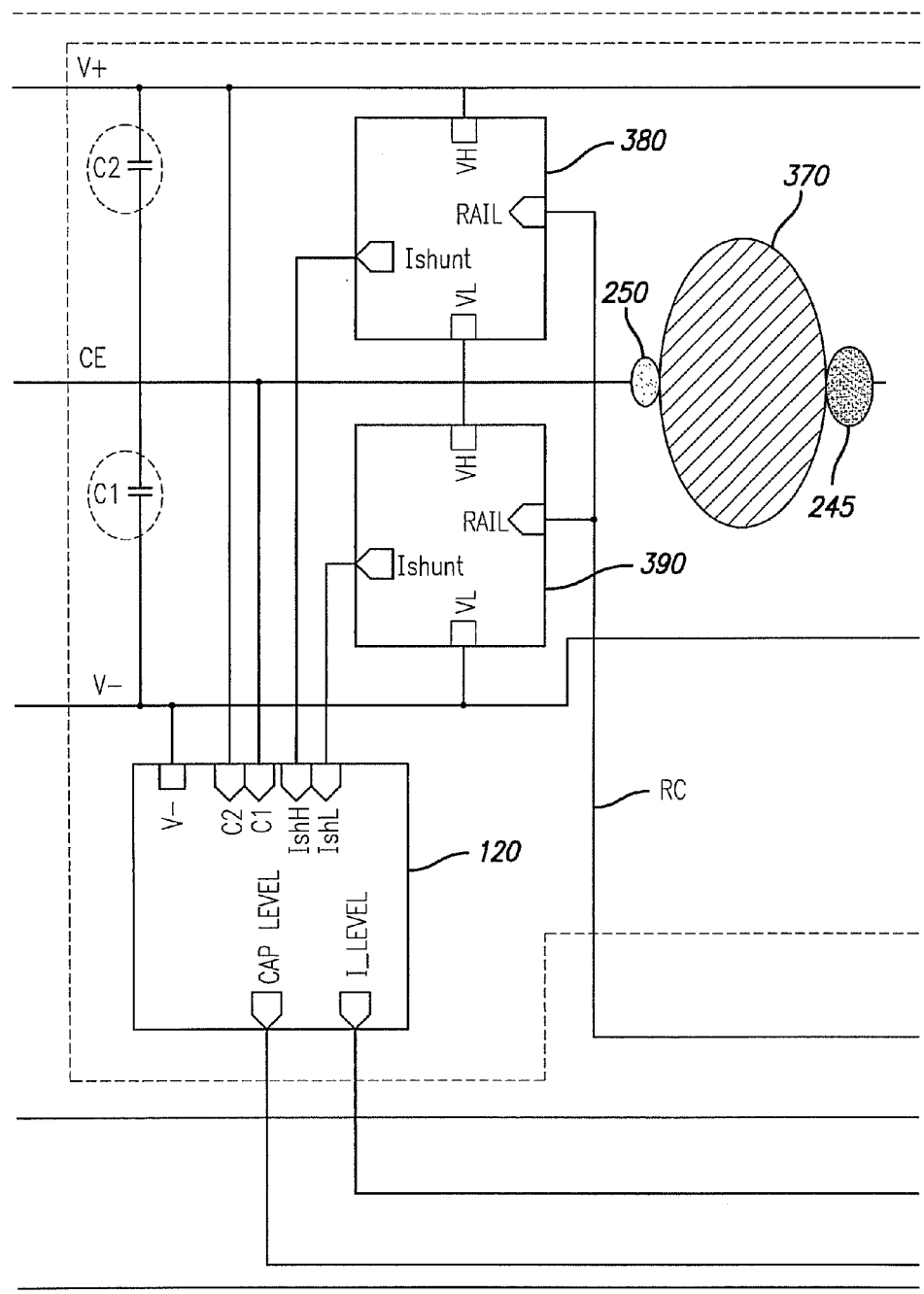
Figure 12C:
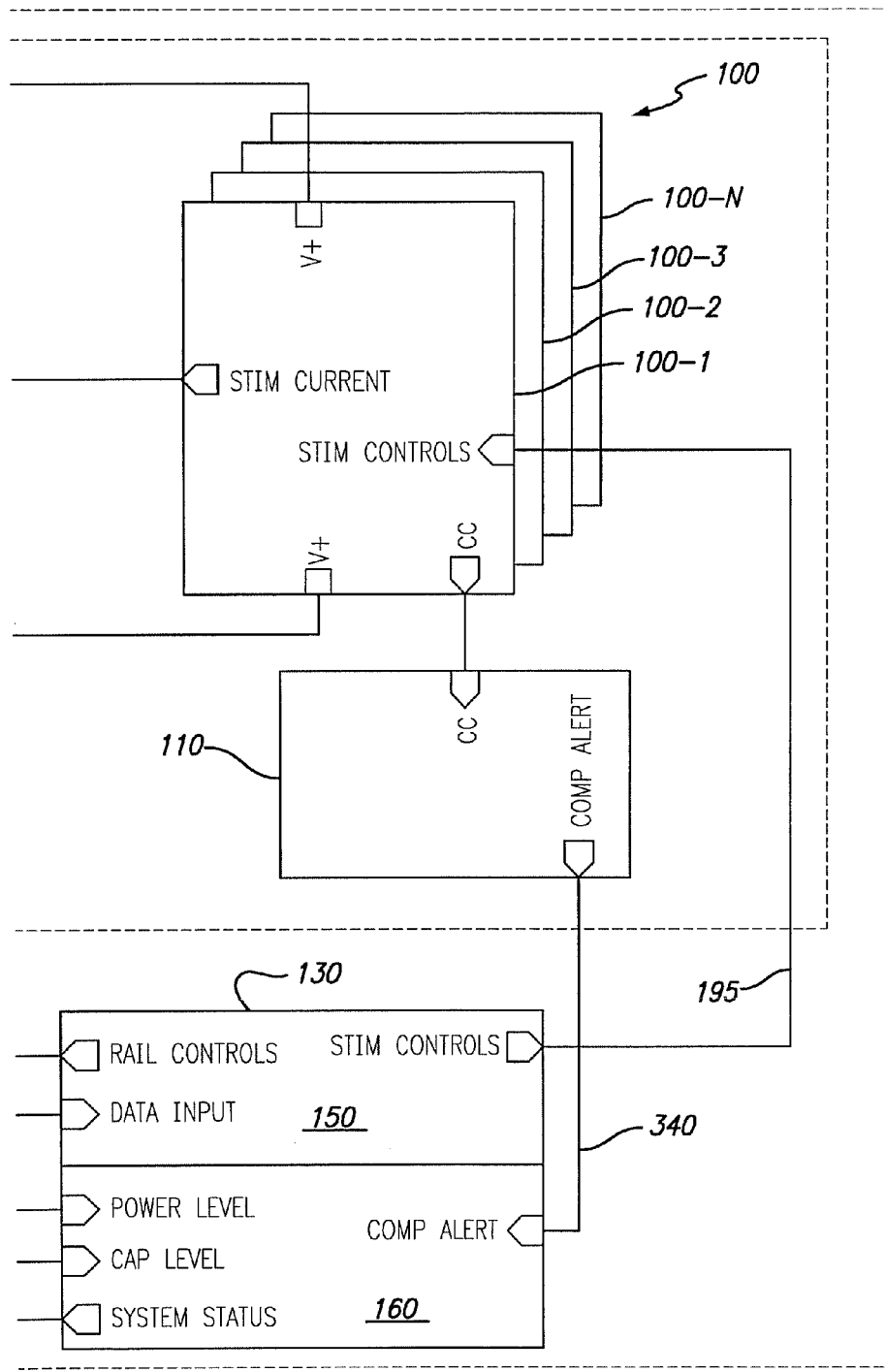

FIGS. 12 A-C show a diagram of an implant power control scheme necessary to derive the shunt regulator (Isrh) signal use in the signal strength indicator.

An implant portion of the visual prosthesis 310 receives power from an video processing unit 35 through an inductive power link coupled through coils. Control and status information are exchanged between implanted portion 310 and video processing unit 35 through data link 142.

Power at the implanted portion is received by implant coil 150. Implant coil 150 is tunable with capacitor C3 to the power carrier frequency. The received AC power is converted into DC power by a rectifier circuit 160. Rectifier circuits are known per se to the person skilled in the art. In the case at issue, the rectifier circuit 160 can comprise, by way of example, diode bridges or MOSFET circuits.

The output V+, VM, V− of rectifier circuit 160 provides the power to deliver controlled stimulation currents to the tissue 370. A small portion of the output of rectifier 160 can be tapped out or diverted to supply circuits for other operations through a regulator circuit 175. Such operations can include RF data receiving and transmitting, logic control, signal measurements and so on.

The output of rectifier circuit 160 continuously charges two capacitive storage arrangements which are shown as C1 and C2 in FIG. 12 B provided to supply all electrode drivers for bi-phase or multi-phase stimulation. Those capacitive arrangements could also be represented as arrays of capacitors or storage devices based on a capacitive behavior to boost output power.

The voltages of C1 and C2 are limited by shunt regulator circuits 380 and 390, respectively. The charge stored on C1 and C2 is transferred to the tissue 370 through a plurality of electrode drivers 100-*i* forming a driver array 100 comprised of electrode drivers 100-1, 100-2, . . . , 100-*i*, . . . 100-*n*. The drivers act as a controlled energy transporter to allow stimulation of the tissue 370 in form of bursts of biphasic (anodic and cathodic) current pulses. Each driver can comprise, for example, a constant current source or sink circuit. Each driver is connected to a respective stimulation electrode 245-*i*. The plurality of stimulation electrodes 245-*i* forms a stimulating electrode array 245 in direct contact with the tissue 370, as shown in FIG. 12B. As also explained above, while the present embodiments makes reference to a retinal tissue, other types of human or animal tissue can be envisaged by the person skilled in the art.

The present disclosure provides for monitoring and control of excessively low capacitor voltage. In particular, when charges are transferred from capacitors C1, C2 to the tissue 370, the voltage on the capacitors drops. A minimum value for this voltage is defined by a so-called compliance voltage. The compliance voltage is defined by the electrode-tissue impedance at the interface 245-370 and the stimulating current 225 flowing between a driver 100-*i* and a respective electrode 245-*i*. If the voltage on C1 and C2 falls too close to the compliance voltage, the respective driver 100-*i* will not be able to maintain the required amplitude of the stimulation current 255.

In order to prevent this from happening, a compliance monitor circuit 110 is provided. Circuit 110 monitors occurrence of the above situation and notifies the video processing unit 35 through the back telemetry 170-180 to lower the stimulation current amplitude 255 by way of external controller 700 and the transceiver 710 and forward data link 142, or increase the capacitor voltage accordingly by way of the external controller 700 and coil driver 720.

The implanted portion 310 is continuously powered and controlled by the video processing unit 35 through the inductive power link and the data link 142, respectively. The video processing unit 35 comprises an external controller 700, a coil driver 720 and a data transceiver 710. The external controller 700 can include an information collector such as a camera in the case of retinal prosthesis, a microphone in the case of cochlear prosthesis, or some other form of sensory devices such as pressure, position or touch sensors for various other neuronal-stimulation applications. The external controller 700 can include a Digital Signal Processing Unit or a similar operation processor to synthesize the sensed information from the sensors and the feedback information from the implanted portion 310 and generate controls accordingly to command the implanted device to deliver appropriate stimulation (amplitude and timing) to the tissue through the data transceiver 710. The data transceiver 710 ensures that the commands from the external controller 700 are delivered to the implanted portion 310 reliably and the feedback from the implanted portion 310 is received correctly. The data transceiver 710 communicates with the implanted portion 310 in predefined communication protocols through its data antenna 730. In the meantime, the coil driver 720 ensures that adequate but not excessive power is delivered to the implanted portion 310 for the intended stimulation intensity.

Also excessively high capacitor voltage is monitored, to avoid use of unnecessary high power to deliver the same charge. In particular, shunt regulators 380 and 390 include a circuital arrangement to program the level of the nominal capacitor voltage to a required value, for further power saving.

A power monitor circuit 120 is further provided, to monitor the charging and draining conditions of the capacitors, so that the video processing unit 35 can optimize the RF powering condition (see coil driver/monitor 720) and also stop stimulation when the implanted portion 310 cannot be adequately powered.

In summary, a visual prosthetic apparatus, or other implantable stimulator with an RF link is provided. The apparatus provides a means for assisting a clinician in adjusting the RF link between the external and the internal coil. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of fitting a medical device comprising:
providing medical device having
an implantable portion including an internal coil; and
an external portion including an
external coil,
an adjustable mounting system supporting the external coil, and
a real time indicia of a inductive coupling strength between the internal coil and
the external coil;
adjusting the position of the external coil to the point greatest signal strength guided by the real time indicia; and
fixing the mounting system to prevent movement of the external coil.

2. The method according to claim 1, wherein the real time indicia is an indicia of signal strength of a signal transmitted from the internal coil to the external coil.

3. The method according to claim 1, wherein the real time indicia is an audible tone.

4. The method according to claim 3, wherein the audible tone is higher in pitch to indicate a stronger inductive coupling strength and lower in pitch to indicate a weaker inductive coupling strength.

5. The method according to claim 1, wherein the adjustable mounting system includes means for fixing the adjustable mounting system at a location of maximum inductive coupling strength.

6. The method according to claim 1, wherein the medical device is a visual prosthesis.

7. The method according to claim 6, wherein the mounting system mounts the external coil to a glasses frame.

* * * * *